United States Patent
Hsiao

(10) Patent No.: US 9,500,358 B2
(45) Date of Patent: Nov. 22, 2016

(54) AROMA DIFFUSING HEATING DEVICE USING AN AROMA CAPSULE

(71) Applicant: Ming Jen Hsiao, Miaoli County (TW)

(72) Inventor: Ming Jen Hsiao, Miaoli County (TW)

( * ) Notice: Subject to any disclaimer, the term of this patent is extended or adjusted under 35 U.S.C. 154(b) by 235 days.

(21) Appl. No.: 14/157,302

(22) Filed: Jan. 16, 2014

(65) Prior Publication Data

US 2014/0133131 A1    May 15, 2014

Related U.S. Application Data

(63) Continuation-in-part of application No. 13/658,820, filed on Oct. 24, 2012, now abandoned, and a continuation-in-part of application No. 13/669,354, filed on Nov. 5, 2012, now Pat. No. 9,109,780, and a continuation-in-part of application No. 13/670,430, filed on Nov. 6, 2012, now Pat. No. 8,938,159.

(51) Int. Cl.

| A61L 9/03 | (2006.01) |
|---|---|
| H05B 3/22 | (2006.01) |
| H05B 3/68 | (2006.01) |
| F21V 33/00 | (2006.01) |
| H05B 3/36 | (2006.01) |

(52) U.S. Cl.
CPC .............. *F21V 33/0092* (2013.01); *A61L 9/03* (2013.01); *A61L 2209/12* (2013.01); *A61L 2209/131* (2013.01); *H05B 3/36* (2013.01)

(58) Field of Classification Search
None
See application file for complete search history.

(56) References Cited

U.S. PATENT DOCUMENTS

| 3,587,968 A | 6/1971 | Hennart et al. | |
|---|---|---|---|
| 4,731,522 A * | 3/1988 | Manchester | A01M 1/2077 219/433 |
| 5,647,052 A * | 7/1997 | Patel | A61L 9/03 392/390 |
| 6,085,026 A | 7/2000 | Hammons | |
| 6,435,563 B2 | 8/2002 | Phillips | |
| 6,627,857 B1 * | 9/2003 | Tanner | A61L 9/03 219/445.1 |
| D604,699 S | 11/2009 | Yamamoto | |
| 8,068,725 B2 | 11/2011 | Cheung | |
| 8,262,277 B2 * | 9/2012 | Hsiao | A61L 9/03 362/643 |
| 8,265,465 B2 | 9/2012 | Jögensen | |
| D692,548 S | 10/2013 | Hsiao | |
| D692,550 S | 10/2013 | Hsiao | |
| 8,765,073 B1 * | 7/2014 | Hsiao | A61L 2/00 239/34 |
| 8,983,277 B2 * | 3/2015 | Hsiao | A61L 9/16 392/386 |

(Continued)

FOREIGN PATENT DOCUMENTS

| AU | 2012101327 | 1/2013 |
|---|---|---|
| EP | 0321729 | 6/1989 |

(Continued)

*Primary Examiner* — Joseph M Pelham
(74) *Attorney, Agent, or Firm* — Ming Chow; Sinorica, LLC

(57) ABSTRACT

An aroma-diffusing heating device using an aroma capsule is provided, including a hollow housing, a heat conduction container and a heating element. The heat conduction container is disposed in the hollow housing. The heating element is disposed on a bottom side of the heat conduction container. The heat conduction container has an aroma capsule placed therein from a free end thereof. The hollow housing has a funnel-shaped space formed between a slanting slide portion and a protruding edge of a disposable container of the aroma capsule to define an operation space. A user is allowed to grab the protruding edge of the aroma capsule with his fingers and place the aroma capsule in the heat conduction container, and his fingers can slide through the slanting slide portion into the operation space. Therefore, the fingers can enter into and leave from the operation space easily.

19 Claims, 6 Drawing Sheets

(56) References Cited

U.S. PATENT DOCUMENTS

| | | | | |
|---|---|---|---|---|
| 2005/0016985 A1* | 1/2005 | Haas | ............... | A61L 9/03 219/438 |
| 2014/0072286 A1* | 3/2014 | Hsiao | ............... | A61L 9/03 392/390 |
| 2014/0124594 A1* | 5/2014 | Hsiao | ............... | A61L 9/03 239/135 |
| 2014/0126892 A1* | 5/2014 | Hsiao | ............ | B60H 3/0007 392/394 |
| 2014/0133841 A1* | 5/2014 | Hsiao | ............... | A61L 9/03 392/386 |
| 2014/0161674 A1* | 6/2014 | Hsiao | ............... | A61L 9/03 422/125 |
| 2015/0109823 A1* | 4/2015 | Hsiao | ............... | A61L 9/03 362/643 |
| 2015/0117056 A1* | 4/2015 | Hsiao | ............ | F21V 33/0004 362/611 |

FOREIGN PATENT DOCUMENTS

| EP | 1473046 | 11/2004 | | |
|---|---|---|---|---|
| EP | 1627647 | 2/2006 | | |
| EP | 2067491 | 6/2009 | | |
| JP | 2002369705 | 12/2002 | | |
| VG | DE 202013101904 U1 * | 6/2013 | ............... | A61L 9/03 |

* cited by examiner

AROMA DIFFUSING HEATING DEVICE USING AN AROMA CAPSULE

CROSS-REFERENCES TO RELATED APPLICATION

The present invention is a continuation-in-part of U.S. patent application Ser. No. 13/658,820 filed on Oct. 24, 2012, Ser. No. 13/669,354 filed on Nov. 5, 2012, and Ser. No. 13/670,430 filed on Nov. 6, 2012.

BACKGROUND OF THE INVENTION

1. Field of the Invention

This invention relates to an aroma-diffusing heating device having an aroma capsule.

2. Description of Related Art

U.S. Pat. Nos. 8,066,420, 8,262,277 and 8,147,116 disclose an aroma-diffusing heating device, which includes a power supply, a heating source, essential oil or aroma wax, and a container for the aroma wax to be contained therein. The essential oil is likely to be leaked from the container as the container is toppled over. After the aroma wax contained in the container is evaporated completely and before new aroma wax is placed in the container, a user needs to take aroma wax residues out from the container and clean the container. During the cleaning process, the user is likely to be stained by the aroma wax residues.

SUMMARY OF THE INVENTION

In view of the problems of the prior art, the present invention provides an aroma-diffusing heating device using an aroma capsule. The aroma-diffusing heating device can be simply and smoothly combined with a disposable aroma capsule. An aroma in the aroma capsule, even if the aroma-diffusing heating device is toppled by accidence, will not flow to a region outside of the aroma capsule. Since the aroma capsule is disposable, a new aroma capsule can replace the used aroma capsule easily.

An aroma-diffusing heating device using an aroma capsule according to the present invention comprises: a hollow housing, a heat conduction container and a heating element, wherein the hollow housing comprises a hole, a first opening and a second opening, the heat conduction container is disposed in the hollow housing, the heat conduction container has a free end facing toward the first opening, the heating element is disposed on a bottom side of the heat conduction container, and the heating element is connectible to a power unit that heats up the heat conduction container of the aroma-diffusing heating device.

A user is allowed to place an aroma capsule in the heat conduction container through a free end of the heat conduction container. A power source (not shown) provides power to the heating element, and the heating element generates heat that heats up the heat conduction container and the aroma capsule, for the aroma in the aroma capsule to diffuse fragrance upward.

The heat conduction container further comprises a screw frame disposed on a bottom side of the heat conduction container, the screw frame comprises a fixture hole, the aroma-diffusing heating device further comprises a cushion pad, a screw rod and a bottom cover, the bottom cover is disposed on the other side of the hollow housing, the heating element props against a bottom portion of the heat conduction container, the heating element has an outer side combined with the cushion pad, the screw rod has one side passing through the bottom cover and the other side passing through the fixture hole and propping against the cushion pad to push the heating element upward such that the heating element is in close contact with a bottom portion of the heat conduction container and transfers heat to the heat conduction container stably.

The cushion pad is U-shaped and mounted to an outer portion of the heating element and a bottom side of the screw frame, without moving with respect to the heating element.

The heating element is a PTC thermal resistor, the cushion pad protects the heating element from being cracked and prevents a portion of heat generated by the heating element from being transferred externally.

The aroma-diffusing heating device further comprises a light guiding member and a light-emitting device, the hollow housing further comprises a plurality of holes, the light guiding member is disposed on an inner side of the hollow housing, the light-emitting device is disposed on an inner side of the light guiding member, the light-emitting device is connectible to a power source, light emitted by the light-emitting device is projected onto the light guiding member to generate a halo effect, and the light is diffused through the holes to a region outside of the aroma-diffusing heating device.

The hollow housing further comprises a slanting slide portion and an inner flange, the slanting slide portion extends from an upper end edge of the hollow housing protrusively downward to an inner portion of the hollow housing, the inner flange extends horizontally from the slanting slide portion, and the heat conduction container is disposed on the inner flange.

The aroma-diffusing heating device further comprises an aroma capsule placed in the heat conduction container, the aroma capsule comprises a disposable container and an aroma, the disposable container comprises an opening and a protruding edge, the protruding edge extends outward from the opening, and the aroma is placed in the disposable container.

The disposable container of the aroma capsule has a bottom side that is placed in the heat conduction container of the aroma-diffusing heating device, and a funnel-shaped space formed between the slanting slide portion and the protruding edge of the disposable container of the aroma capsule defines an operation space.

The aroma is an aroma wax. The aroma capsule further comprises a breathing film mounted to the opening of the disposable container.

Therefore, a user is allowed to grab the protruding edge of the disposable container of the aroma capsule with his fingers, and place the disposable container in the heat conduction container of the aroma-diffusing heating device. A funnel-shaped space that is formed between the slanting slide portion and the protruding edge of the disposable container of the aroma capsule is defined as an operation space. The user may use his fingers to grab the protruding edge of the disposable container of the aroma capsule and place the aroma capsule into the heat conduction container, and slide his fingers into the operation space. The fingers can enter into and leave from the operation space freely. After the aroma in the aroma capsule volatiles completely, the user may reach his index or middle finger through the slanting slide portion into the operation space and prop against the bottom side of the protruding edge of the disposable container, and use his thumb to press against the top side of the protruding edge. The disposable container of the aroma capsule can thus be taken out easily, and a new aroma capsule with an aroma of different fragrance can be placed in the aroma-diffusing heating device quickly.

BRIEF DESCRIPTION OF DRAWINGS

The invention can be more fully understood by reading the following detailed description of the preferred embodiments, with reference made to the accompanying drawings, wherein.

DETAILED DESCRIPTION OF THE INVENTION

Figure 1:
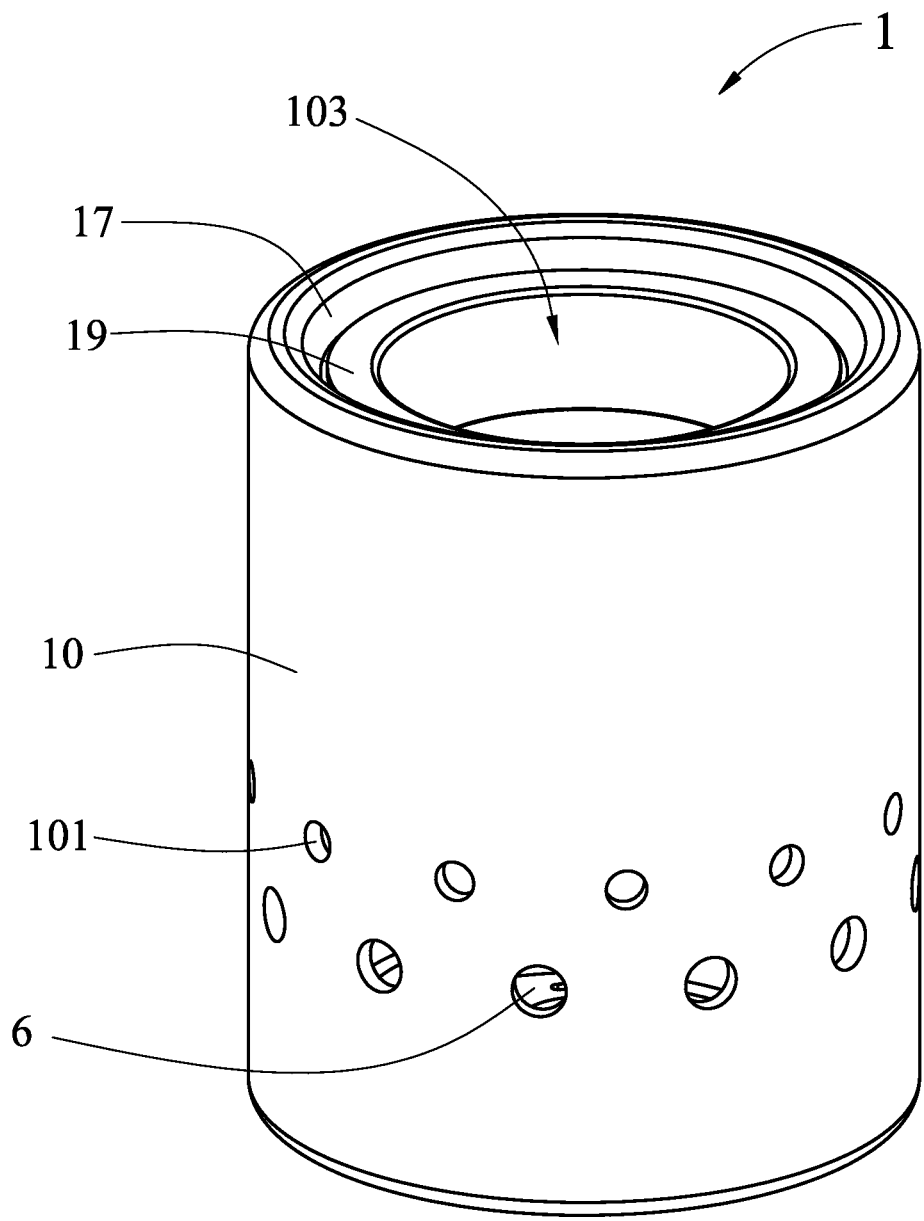
FIG. 1 is a schematic diagram of an aroma-diffusing heating device having an aroma capsule according to the present invention.

The following illustrative embodiments are provided to illustrate the disclosure of the present invention, these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

Refer to FIGS. 1-4. In an embodiment according to the present invention, an aroma-diffusing heating device 1 having an aroma capsule comprises a hollow housing 10, a heat conduction container 11, and a heating element 3. The hollow housing 1 comprises a first opening 103 and a second opening 105. The heat conduction container 11 is disposed on one side of the hollow housing 10. The heat conduction container 11 has a free end 111 facing toward the first opening 11. The heating element 3 is disposed on a bottom side of the heat conduction container 11. The heating element 3 is connectible to a power unit (now shown) that heats the heat conduction container 11.

An aroma capsule 12 can be placed in the heat conduction container 11 from the free end 111. The power unit provides power to the heating element 3, and the heating element 3 generates heat to heat up the heat conduction container 11, such that the aroma capsule 12 generates fragrance and the fragrance is diffused upward through the free end 111.

The heat conduction container 11 comprises a screw frame 113 on a bottom side thereof. The screw frame 113 comprises a fixture hole. The aroma-diffusing heating device 1 further comprises a cushion pad 20, a screw rod 30, and a bottom cover 15. The bottom cover 15 is disposed on the other side of the hollow housing 10. The heating element 3 props against a bottom portion of the heat conduction container 11. The cushion pad 20 is disposed on an outer side of the heating element 3. The screw rod 30 has one side combined with the bottom cover 15, and the other side passing through the fixture hole 115 and propping against the cushion pad 20 to push the heating element 3 upward such that the heating element 3 is in close contact with the bottom portion of the heat conduction container 11 and provides the heat to the heat conduction container 11 stably.

The heat conduction container 11 is made of a heat conduction material. The heat conduction container 11 is made of metal, ceramic or glass. The heating element 3 thus can conduct the heat generated to the heat conduction container 11. The hollow housing 10, if made of ceramic, which, though conducting heat, is a well insulating material, can be used in an aroma-diffusing heating device that operates in a low temperature. The heat conduction container 11 is in a shape that adapts to the aroma capsule 12. The aroma capsule 12 has a housing made of metal film and contains aroma wax or essential oil therein. Since the general aroma, such as aroma wax and essential oil, can diffuse fragrance in a low temperature, e.g., 40-80° C., the heat conduction container 11 can enclose the aroma capsule 12 from a bottom surface or side surface thereof, and thus has a great enough heat conduction area. Upon turning on the aroma-diffusing heating device, the aroma capsule 12 can be heated up and diffuse fragrance very soon. As a result, the aroma-diffusing heating device does not consume much power. Since operating in a moderate temperature, the heat conduction container 11 will not generate much heat, and the aroma in the aroma capsule 12 will not volatile quickly.

In an embodiment, the cushion pad 20 is U-shaped. The U-shaped cushion pad 20 is mounted to an outside portion of the heating element 3 and disposed on the bottom side of the screw frame 113. Therefore, the heating element 3 is fixed and cannot move easily. The heating element 3 is a resistor or other electrically heating element. In an embodiment, the heating element 3 is a PTC. The cushion pad 31 protects the heating element 3 from being cracked, and prevents a portion of heat generated by the heating element 3 from being transferred to the hollow housing 10 or a circuit board. The hollow housing 10 is not heated up directly.

The aroma-diffusing heating device 1 further comprises a circuit board (PCB) (not shown) disposed in the hollow housing 10 and electrically connected to the heating element 3 for providing power to the heating element 3.

Figure 2:
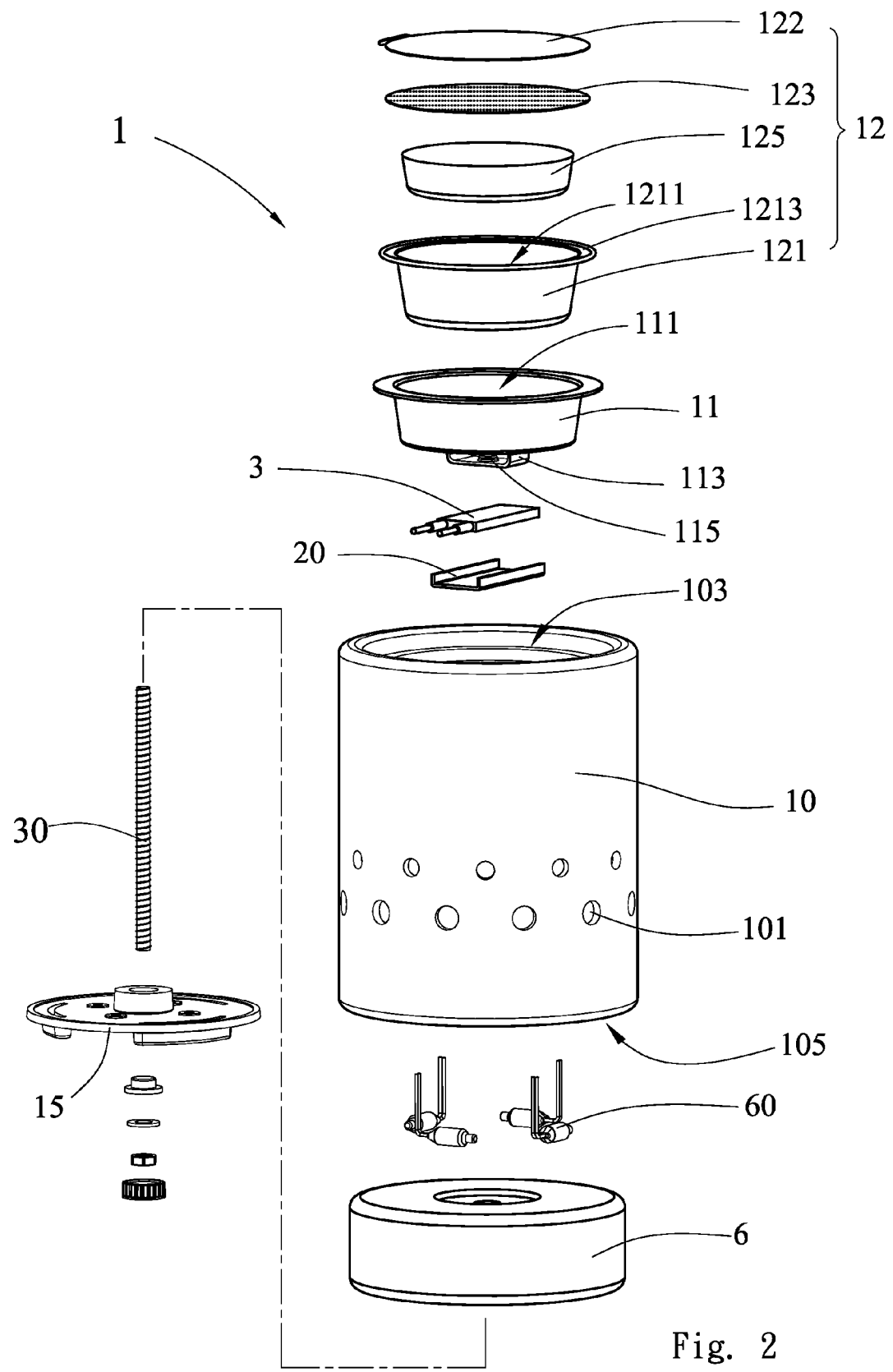
FIG. 2 is an exploded view of an aroma-diffusing heating device having an aroma capsule according to the present invention.
Figure 3:
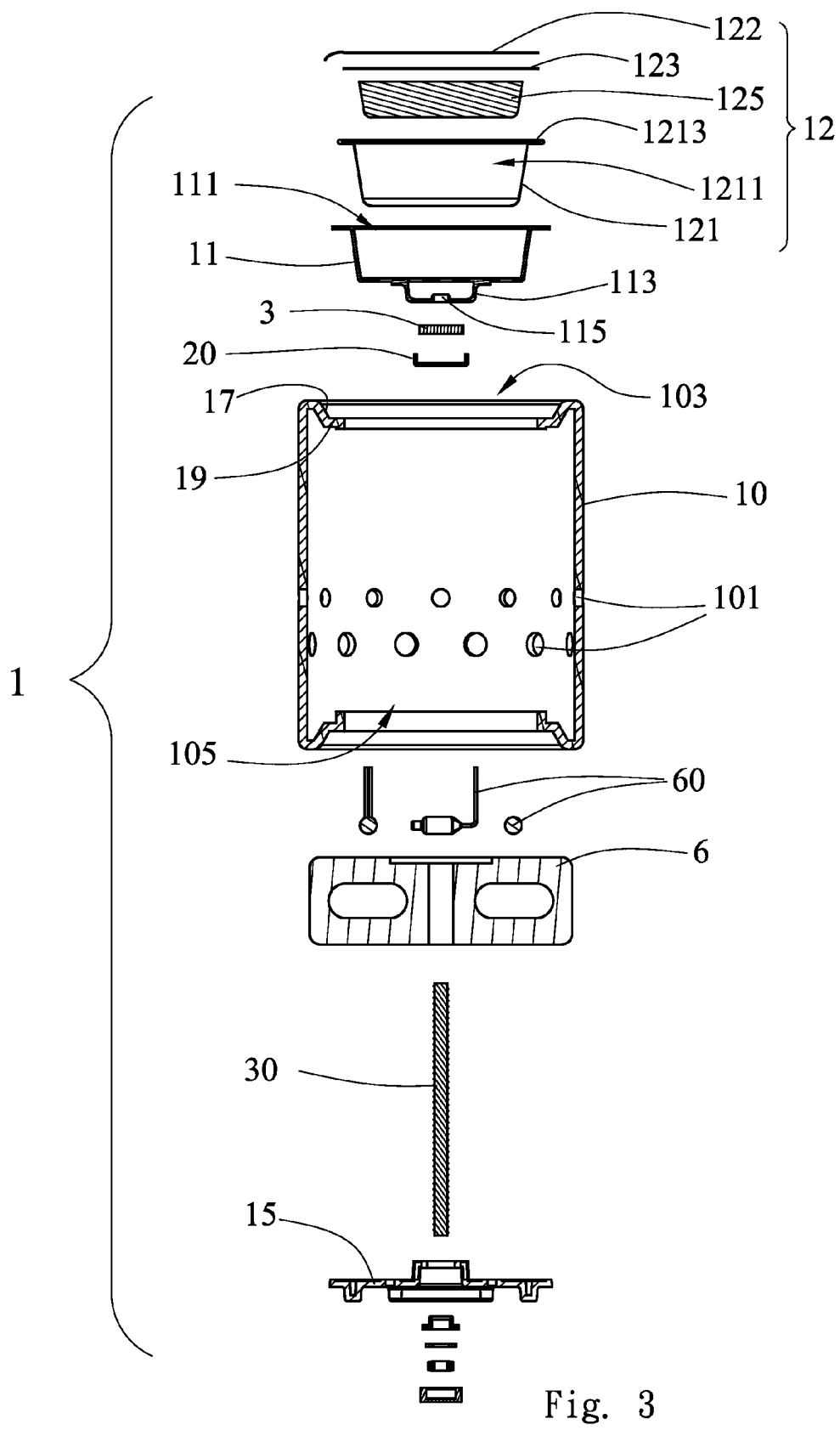
FIG. 3 is a cross-sectional view of an aroma-diffusing heating device having an aroma capsule according to the present invention.
Figure 4:
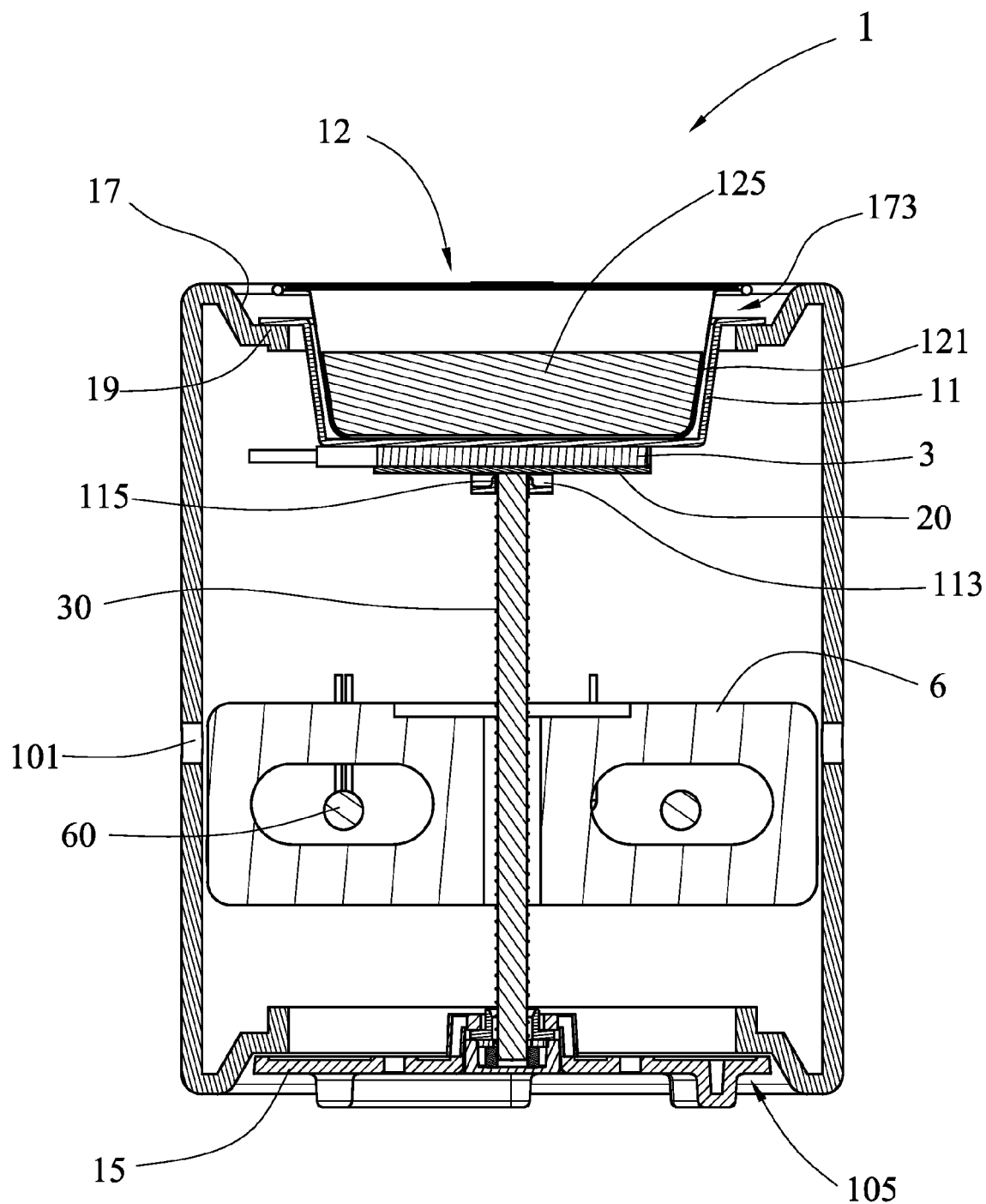
FIG. 4 is another cross-sectional view of an aroma-diffusing heating device having an aroma capsule according to the present invention.
Figure 5:
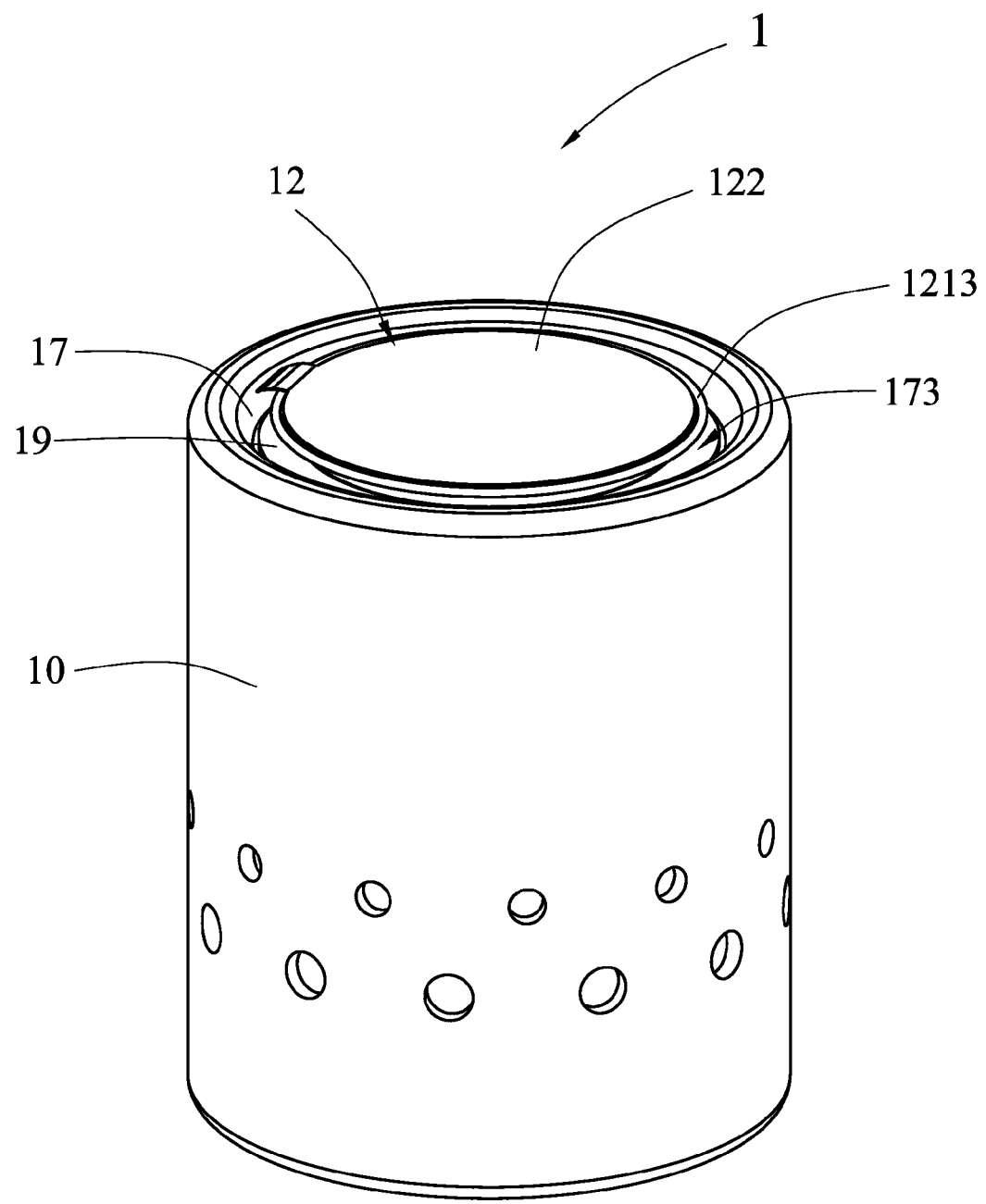
FIG. 5 is an assembled view of an aroma-diffusing heating device having an aroma capsule and an aroma capsule according to the present invention.

Please refer to FIGS. 2-4 at the same time. In an embodiment according to the present invention, the aroma-diffusing heating device 1 further comprises a light guiding member 6 and a light-emitting device 60. The hollow housing 10 further comprises a plurality of holes 101. The light guiding member 6 is disposed on an inner side of the hollow housing 10. The light-emitting device 60 is disposed on an inner side of the light guiding member 6. In an embodiment, the light-emitting device 60 can be connected to an external power supply, or to the power provided by the circuit board. When the light emitted by the light-emitting device 60 is projected onto the light guiding member 6, a halo effect occurs. The aroma capsule diffuses fragrance through the holes 101 to a region outside of the aroma-diffusing heating device 1. The light-emitting device 60 can be used as a night lamp, or remind a user that the aroma-diffusing heating device is in operation. In an embodiment, the light guiding member 6 is made of a hallow silicon material that is thermally resistant.

Refer to FIGS. 3-6. In an embodiment, the hollow housing 10 further comprises a slanting slide portion 17 and an inner flange 19. The slanting slide portion 17 extends protrusively downward from an upper end edge 171 toward an inner portion of the hollow housing 10. The inner flange 19 extends horizontally from the slanting slide portion 17. The heat conduction container 11 is disposed on the inner flange 19.

The aroma-diffusing heating device 1 further has an aroma capsule 12. The aroma capsule 12 is placed in the heat conduction container 11. The aroma capsule 12 further comprises a disposable container 121 and an aroma 125. The disposable container 121 comprises an opening 1211 and a protruding edge 1213. The protruding edge 1213 extends outward from the opening 1211. The protruding edge 1213 allows the user to move and operate the aroma capsule 12 easily and conveniently. The aroma 125 is placed in the disposable container 121. The aroma 125 is, for example, an aroma wax, essential oil, aroma block, or aroma stone. In an embodiment, the aroma 125 is an aroma. The heating element 3 is electrically connected to a power supply and generates heat, which is transferred to the heat conduction container 11 and to the disposable container 121, for the aroma 125 to diffuse fragrance.

Figure 6:
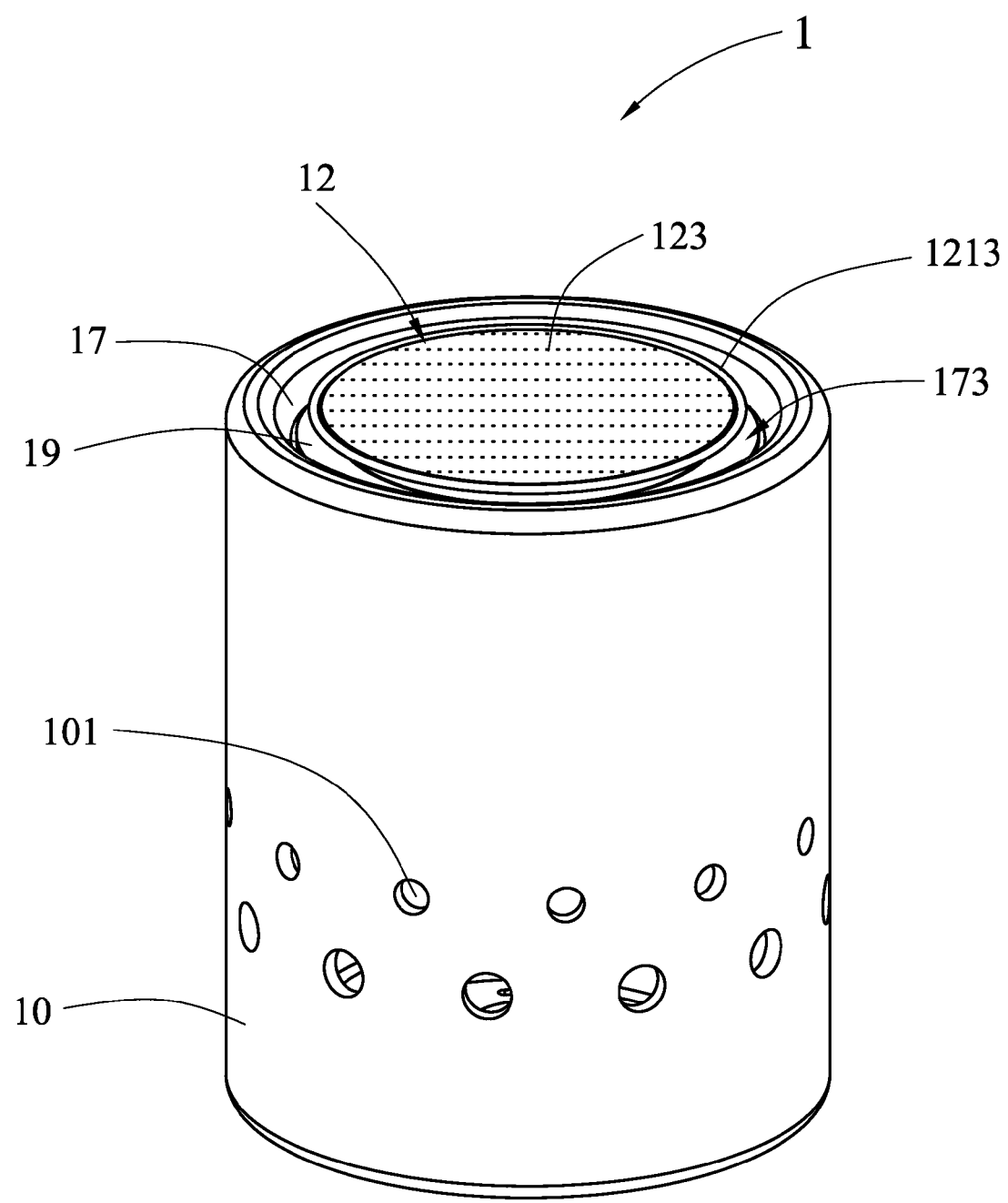
FIG. 6 is an assembled view of aroma-diffusing heating device having an aroma capsule and an aroma capsule with a cover tore off according to the present invention.

Please refer to FIGS. 2, 3 and 6. In a preferred embodiment according to the present invention, the aroma capsule 12 further comprises a breathing film 123 that is mounted to the opening 1211 of the disposable container 121.

Therefore, a user is allowed to grab the protruding edge 1213 of the disposable container 121 of the aroma capsule 12 with his fingers, and place the disposable container 121 in the heat conduction container 11 of the aroma-diffusing heating device 1. A funnel-shaped space that is formed between the slanting slide portion 17 and the protruding edge 1213 of the disposable container 121 of the aroma capsule 12 is defined as an operation space 173. The user may use his fingers to grab the protruding edge 1213 of the disposable container of the aroma capsule 12 and place the aroma capsule into the heat conduction container 11, and slide his fingers into the operation space 173. The fingers can enter into and leave from the operation space 173 freely. After the aroma in the aroma capsule volatiles completely, the user may reach his index or middle finger through the slanting slide portion 17 into the operation space 173 and prop against the bottom side of the protruding edge 1213 of the disposable container 121, and use his thumb to press against the top side of the protruding edge 1213. The disposable container of the aroma capsule can thus be taken out easily, and a new aroma capsule 12 with an aroma of different fragrance can be placed in the aroma-diffusing heating device 1 quickly.

Please refer to FIGS. 2 and 6 at the same time. In an embodiment according to the present invention, the breathing film 123 has venting holes that diffuse the fragrance of the aroma 125 upward into an ambient environment. The breathing film 123 is made of a cloth (e.g., non-woven fabric, fibrous fabric, linen or canvas), fibrous sheets, a breathing film or a porous metal foil. In an embodiment, the breathing film 123 is made of the breathing film. The breathing film 123 has its periphery mounted to the opening 1211 of the disposable container 121. When the aroma-diffusing heating device 1 is toppled by accident, the aroma in the disposable container 121 will be prevented by the breathing film 123 from flowing into the car or other regions in the car to contaminate or bring in danger the car.

In an embodiment, in a case in which the aroma capsule 12 is not combined with the breathing film 123 or is combined with the breathing film 123, the aroma capsule 12 further comprises a sealing cover 122 mounted to the opening 1211 of the disposable container 121, for preventing the aroma 125 in the aroma capsule 12 from being contaminated or losing its fragrance during a shipping process. The sealing cover 72 can be tore off first, and then the aroma capsule 12 can be placed in the heat conduction container 11.

The disposable container 121 is made of metal, hard plastic, fibrous bowl (e.g., plant fiber such as corn fiber, glass fiber and carbon fiber) or composite material.

In an embodiment, the disposable container 121 is an aluminum foil bowl that is made of metal such as aluminum foil. Therefore, the disposable container 121 is thin and light, and has a well enough heat conducting capability to transferring the heat generated by the heating element 3 to the disposable container 121 and the aroma 125, for the aroma 125 to be heated up and diffuse fragrance. The aluminum disposable container 121 is tough, unlike the conventional container, which is made of a fragile material such as ceramic and glass.

Refer to FIGS. 2, 3 and 6. Since the aroma 125 is placed in the disposable container 121, rather than in a conventional container, the user is allowed to tear off the sealing cover 122 (referring to FIGS. 5 and 6), and then place the aroma capsule 12 in the heat conduction container 11, without worrying about being contaminated by the aroma 125. After the aroma 125 volatiles through the free end 111 of the heat conduction container 11 completely, the disposable container 121 can be removed from the heat conduction container 11 through the free end 121, and a new aroma capsule 12 with different aroma can be placed in the heat conduction container 11, without the need of washing the disposable container 121. Since the outer housing of the disposable container 121 is made of an aluminum foil, the user does not need to worry about breaking or washing the disposable container 121. An additional container for the aroma 125 to be accommodated therein is not necessary.

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:

1. An aroma-diffusing heating device using an aroma capsule, comprising:
   a hollow housing;
   a heat conduction container;
   a heating element;
   the hollow housing comprises a first opening at one end of the hollow housing and a second opening at an opposite end of the hollow housing;
   the heat conduction container is disposed in the hollow housing;
   the heat conduction container has an open end facing toward the first opening;
   the heating element is disposed against the exterior bottom of the heat conduction container;
   the heating element is connectible to a power unit that heats up the heat conduction container of the aroma-diffusing heating device;
   the hollow housing further comprises a slanting slide portion and an inner flange;
   the slanting slide portion extends from an upper end edge of the hollow housing protrusively downward to an inner portion of the hollow housing;
   the inner flange extends horizontally from the slanting slide portion, and the heat conduction container is disposed on the inner flange.

2. The aroma-diffusing heating device of claim 1, wherein the heat conduction container further comprises:
- a screw frame is disposed on a bottom side of the heat conduction container;
- the screw frame comprises a fixture hole;
- the aroma-diffusing heating device further comprises a cushion pad, a screw rod and a bottom cover;
- the bottom cover is disposed on one side of the hollow housing;
- the heating element props against a bottom portion of the heat conduction container;
- the heating element has an outer side confronting the cushion pad;
- the screw rod has one end passing through the bottom cover and the other end passing through the fixture hole and propping against the cushion pad to push the heating element upward such that the heating element is in close contact with a bottom portion of the heat conduction container and transfers heat to the heat conduction container stably.

3. The aroma-diffusing heating device of claim 2, wherein the cushion pad is U-shaped and is mounted to the heating element.

4. The aroma-diffusing heating device of claim 3, wherein the heating element is a PTC thermal resistor, the cushion pad protects the heating element from being cracked and prevents a portion of heat generated by the heating element from being transferred externally.

5. The aroma-diffusing heating device of claim 4, wherein the aroma-diffusing heating device further comprises a light guiding member and a light-emitting device, the hollow housing further comprises a plurality of holes, the light guiding member is disposed on an inner side of the hollow housing, the light-emitting device is disposed on an inner side of the light guiding member, the light-emitting device is connectible to a power source, light emitted by the light-emitting device is projected onto the light guiding member to generate a halo effect, and the light is diffused through the holes to a region outside of the aroma-diffusing heating device.

6. The aroma-diffusing heating device of claim 1, wherein the aroma-diffusing heating device further comprises an aroma capsule placed in the heat conduction container, the aroma capsule comprises a disposable container and an aroma, the disposable container comprises an opening and a protruding edge, the protruding edge extends outward from the opening, and the aroma is placed in the disposable container.

7. The aroma-diffusing heating device of claim 6, wherein the disposable container of the aroma capsule has a bottom side that is placed in the heat conduction container of the aroma-diffusing heating device, and a funnel-shaped space formed between the slanting slide portion and the protruding edge of the disposable container of the aroma capsule defines an operation space.

8. The aroma-diffusing heating device of claim 6, wherein the aroma is an aroma wax.

9. The aroma-diffusing heating device of claim 7, wherein the aroma is an aroma wax.

10. The aroma-diffusing heating device of claim 6, wherein the aroma capsule further comprises a breathing film mounted to the opening of the disposable container.

11. The aroma-diffusing heating device of claim 7, wherein the aroma capsule further comprises a breathing film mounted to the opening of the disposable container.

12. The aroma-diffusing heating device of claim 8, wherein the aroma capsule further comprises a breathing film mounted to the opening of the disposable container.

13. The aroma-diffusing heating device of claim 2, wherein the hollow housing further comprises a slanting slide portion and an inner flange, the slanting slide portion extends from an upper end edge of the hollow housing protrusively downward to an inner portion of the hollow housing, the inner flange extends horizontally from the slanting slide portion, and the heat conduction container is disposed on the inner flange.

14. The aroma-diffusing heating device of claim 13, wherein the aroma-diffusing heating device further comprises an aroma capsule placed in the heat conduction container, the aroma capsule comprises a disposable container and an aroma, the disposable container comprises an opening and a protruding edge, the protruding edge extends outward from the opening, and the aroma is placed in the disposable container.

15. The aroma-diffusing heating device of claim 14, wherein the disposable container of the aroma capsule has a bottom side that is placed in the heat conduction container of the aroma-diffusing heating device, and a funnel-shaped space formed between the slanting slide portion and the protruding edge of the disposable container of the aroma capsule defines an operation space.

16. The aroma-diffusing heating device of claim 14, wherein the aroma is an aroma wax.

17. The aroma-diffusing heating device of claim 15, wherein the aroma is an aroma wax.

18. The aroma-diffusing heating device of claim 15, wherein the aroma capsule further comprises a breathing film mounted to the opening of the disposable container.

19. The aroma-diffusing heating device of claim 16, wherein the aroma capsule further comprises a breathing film mounted to the opening of the disposable container.

* * * * *